United States Patent

Cerier et al.

Patent Number: 5,100,417
Date of Patent: Mar. 31, 1992

[54] SUTURE ANCHOR AND DRIVER ASSEMBLY

[75] Inventors: Jeffrey C. Cerier, Franklin, Mass.; Russell F. Warren, Greenwich, Conn.; Gerard S. Carlozzi, Weymouth, Mass.

[73] Assignee: American Cyanamid Company, Stamford, Conn.

[21] Appl. No.: 552,440

[22] Filed: Jul. 13, 1990

[51] Int. Cl.⁵ .............................................. A61B 17/00
[52] U.S. Cl. .................................. 606/139; 606/144; 606/232
[58] Field of Search ............... 606/232, 73, 104, 236, 606/86, 65, 220, 170, 139, 144, 145, 233

[56] References Cited

U.S. PATENT DOCUMENTS

| | | | |
|---|---|---|---|
| 2,121,193 | 6/1938 | Hanicke | 606/104 |
| 2,268,755 | 1/1942 | Li | 606/139 |
| 2,329,398 | 9/1943 | Duffy | 606/104 |
| 4,275,717 | 6/1981 | Bolesky | |
| 4,632,100 | 12/1986 | Somers et al. | 606/73 |
| 4,669,473 | 6/1987 | Richards et al. | |
| 4,738,255 | 4/1988 | Goble et al. | 606/86 |
| 4,741,330 | 5/1988 | Hayhurst | 606/232 |
| 4,895,148 | 1/1990 | Bays et al. | 606/213 |
| 4,968,315 | 11/1990 | Gatturna | 606/139 |
| 5,002,550 | 3/1991 | Li | 606/139 |

FOREIGN PATENT DOCUMENTS

| | | | |
|---|---|---|---|
| 2118474 | 11/1983 | United Kingdom | 606/72 |
| 86/03666 | 7/1986 | World Int. Prop. O. | 606/72 |

*Primary Examiner*—Stephen C. Pellegrino
*Assistant Examiner*—Gary Jackson
*Attorney, Agent, or Firm*—Douglas E. Denninger; John A. Artz

[57] ABSTRACT

An anchor and anchor driver device for securely and accurately positioning and installing a bone (suture) anchor in place are disclosed. The bone anchor has a rounded or pointed head and a series of ridges around it which are used to help force fit the anchor into a hole and to hold it in place. A suture is positioned through the anchor for subsequent use during the surgical procedure. The driver device has a handle and elongated shaft and is used to position and install the anchor in place. The anchor snap fits onto the end of the shaft over an anti-rotation pin which mates with slots in the anchor. The ends of the suture are affixed to the driver handle. Means are provided on the driver to prevent the suture from interfering with the positioning and installation procedure.

8 Claims, 2 Drawing Sheets

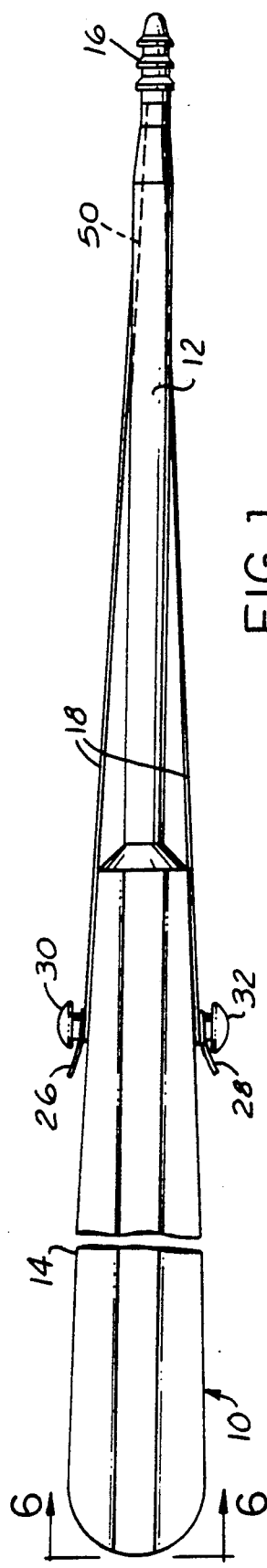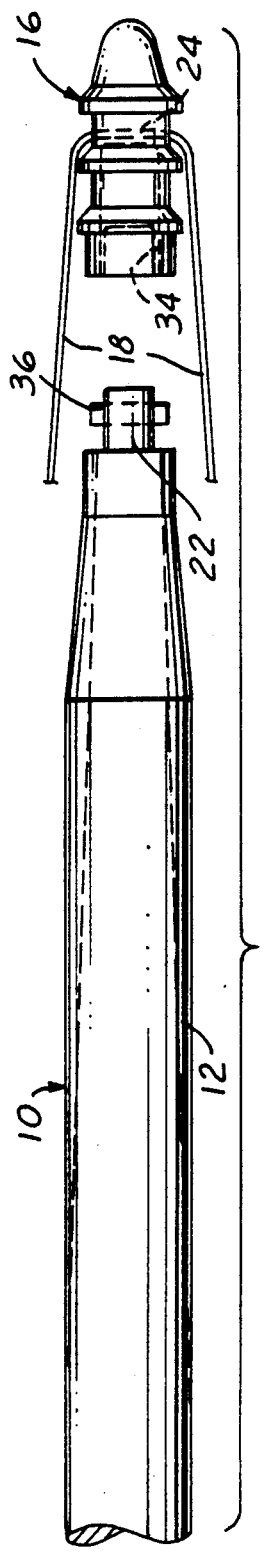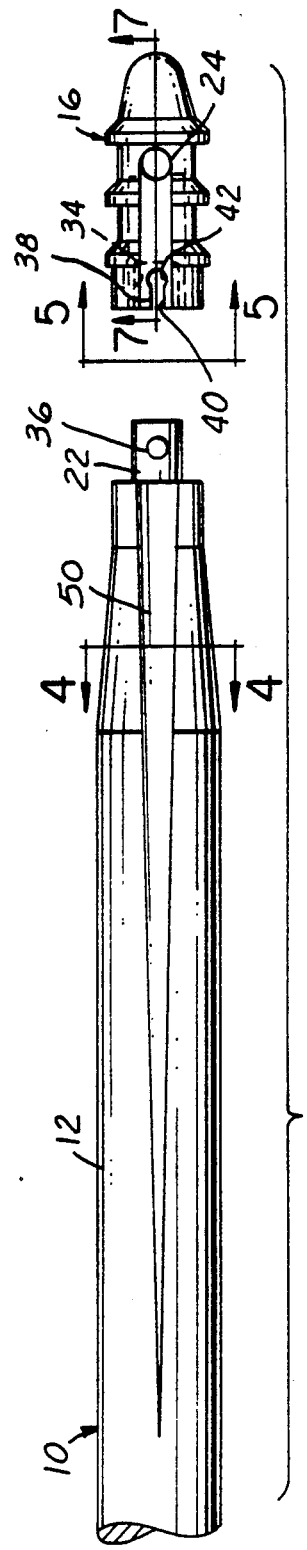

SUTURE ANCHOR AND DRIVER ASSEMBLY

TECHNICAL FIELD

A suture anchor for implanting in bone or tissue for surgical use is disclosed. The anchor is securely affixed on the end of a driver device and positioned and installed during surgery.

BACKGROUND ART

Anchoring or affixation devices and systems for medical or surgical use are in common use today. The anchors are implanted to aid in holding bone, tissue, ligaments and the like together or in place until healing takes place, or are used temporarily to help perform a procedure necessary for optimum surgical results. When implanted permanently, the anchors can be made from an absorbable material if desired.

Bone and suture anchors are used, for example, during orthopedic surgery to hold fractured bones together, affix ligaments to bones and to aid in determining isometric placement of anterior cruciate ligament replacements. Examples of such anchors are shown in U.S. Pat. Nos. 4,537,185, 4,632,100, 4,640,271, 4,723,541 and 4,738,255.

Some positioning and driver mechanisms and systems are known which are used to accurately position and install the bone anchors in place. Examples of such mechanisms and systems are disclosed, for example, in U.S. Pat. Nos. 3,990,438, 4,537,185, 4,632,100, 4,723,541 and 4,738,255. Two other the "Statak" mechanism marketed by Zimmer, Inc., Warsaw, IN and the "Isotac" mechanism marketed by Acufex Microsurgical, Inc., Norwood, MA.

It is an object of the present invention to provide an improved bone or suture anchor for surgical use. It is another object of the present invention to provide an improved driver device for a bone or suture anchor.

It is a still further object of the invention to provide a surgical anchor and driver assembly which allows efficient and accurate positioning and placement of a bone or suture anchor during surgery, the anchor being able to be affixed either for permanent or temporary use, and the driver being able to remove the installed anchor if desired.

It is also an object of the invention to provide an anchor and driver assembly in which the bone or suture anchor can be temporary securely affixed to the driver device for installation and removal, and be removed easily from the driver device when desired. It is another object to provide means on the driver device to hold the anchor temporarily in place and prevent it from rotating relative to the driver device.

It is still another object to provide a surgical bone or suture anchor and driver assembly in which sutures holding the anchor in place are recessed or positioned in a way not to obstruct or cause a problem during positioning, installation and/or removal of the anchor.

These and other objects are met by the present invention which will become apparent upon review of the following detailed description of the invention, when taken by itself or in view of the drawings.

DISCLOSURE OF INVENTION

The present invention relates to a unique and improved anchor, an anchor driver device, and a combined anchor and driver assembly. The anchor is a bone or suture anchor with a rounded, conical or pointed tip and one or more ridges around its circumference which are used to help install (force fit) the anchor into a previously drilled hole in bone or tissue. The ridges act to hold the anchor in position in the hole for its intended use. Preferably, a suture is positioned through a hole in the anchor and extends from the anchor for subsequent use by the surgeon (for example, to hold ligaments, bones or tissue in place, or for use during isometric testing of the positioning for a substitute anterior cruciate ligament).

The anchor is adapted to be securely positioned on the end of a driver device. The driver has a handle and elongated shaft. The anchor snaps or force fits onto the end of the shaft and is keyed against rotation. The suture is affixed to the handle of the driver and grooves or slots are provided along the driver shaft for positioning of the sutures during use of the anchor and driver assembly. By positioning the sutures in the grooves, they are placed out of the way so they cannot interfere with positioning, placement, installation or removal of the anchor.

In an alternative embodiment, the anchor is hollow and the driver handle and shaft are cannulated. This allows the sutures to be passed through the anchor and driver and not interfere with the installation or removal procedures.

BRIEF DESCRIPTION OF DRAWINGS

FIG. 1 illustrates the unique anchor and driver assembly with the anchor being positioned and held in place on the driver;

FIG. 2 is a partial exploded view of the anchor and the end of the driver illustrating their features and showing how they are affixed together;

FIG. 3 is a partial exploded view similar to FIG. 2 but with the anchor and driver shaft rotated 90° relative to the view shown in FIG. 2 and with the suture removed for ease of viewing;

BEST MODE FOR CARRYING OUT THE INVENTION

Figure 4:
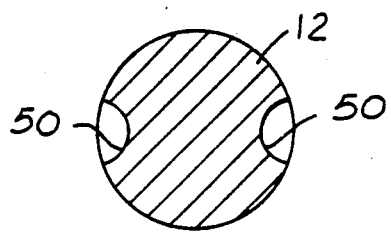
FIG. 4 is a cross-sectional view of the driver shaft taken along lines 4—4 in FIG. 3.

The features and details of the preferred embodiment of the unique anchor and driver assembly are shown in FIGS. 1–7. The driver device is generally designated by the reference numeral 10 and the anchor by the reference numeral 16.

The driver device has a shaft member 12 attached or connected to a handle member 14. The shaft member and handle member can be separate members securely fastened together or they can be made from a single piece of material. Preferably the handle is a hollow stainless tube member having the shape shown in FIGS. 1 and 6 and the shaft is a stainless steel rod which is soldered, welded or otherwise affixed in or to the handle.

The anchor 16 is situated for installation (and also for removal if that is desired) on end projection 22 of the shaft 12, in a manner to be described in more detail below. A suture 18 is positioned through a hole or opening 24 in the anchor 16 and the two ends 26 and 28 of the suture are securely wrapped or tied around fixation posts 30 and 32, respectively. In order to securely hold the sutures which are wrapped on the posts 30 and 32, O-rings (not shown) preferably are positioned on the stems of each of the posts.

The positioning of the anchor 16 on end 22 and the affixation of the suture 18 on the fixation posts 30, 32 tightly and securely holds the anchor on the driver for use during surgery. In this manner, the anchor will not be subject to being dislodged, moved out of position on the shaft or accidently displaced from the shaft while the driver is being used to position and place the anchor during surgery. This is particularly important when the anchor is being used during arthroscopic knee, shoulder or other joint surgery and it would be harmful for the anchor to become loose in the joint.

Figure 5:
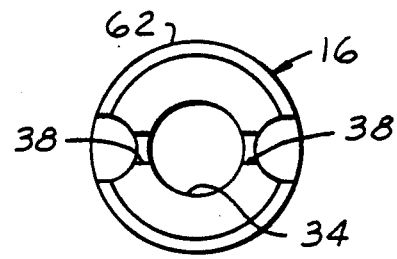
FIG. 5 is an end plan view of the anchor viewed in the direction of the arrows 5—5 in FIG. 3.
Figure 6:
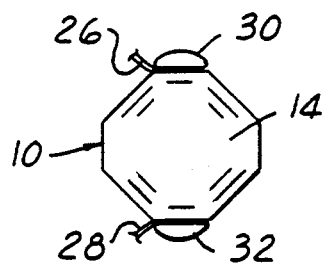
FIG. 6 is an end plan view of the driver device viewed in the direction of the arrows 6—6 in FIG. 1.
Figure 7:
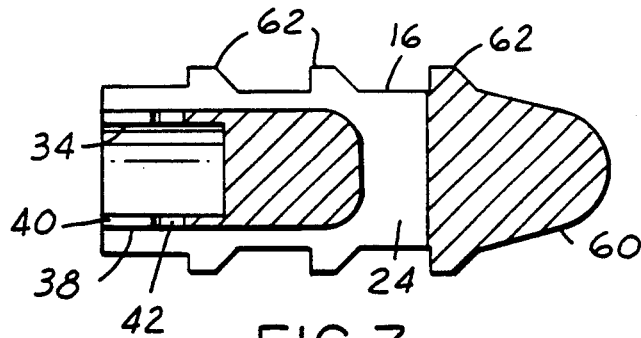
FIG. 7 is a cross-sectional view of the anchor taken along lines 7—7 in FIG. 3.

The end projection 22 is adapted to fit within a mating recess or socket 34 in the anchor 16 (see FIGS. 2, 3 and 5). The cross-sectional size and shape of the projection 22 and socket 34 can be of any common geometric shape, but preferably have the same shape and are circular (as shown by FIG. 5). If desired, the outside diameter of projection 22 and the inside diameter of socket 34 also can be dimensioned such that the two members have a frictional or slight force fit relationship.

A dowel or pin 36 is positioned in end projection 22 substantially perpendicular to the longitudinal axis of the driver device. The pin 36 projects on both sides of the end 22 forming two "ears" or "tabs".

The anchor 16 has a pair of slots 38 which are formed on opposite sides (180° apart) of the end of the anchor which fits on the driver device. The slots 38 are positioned and dimensioned to snap over and onto the protruding ends of the pin 36 on the driver. The slots 38 have an elongated passageway 40 which is slightly smaller in width than the cross-sectional diameter of the pin 36 and a larger generally circular end portion 42 which has substantially the same diameter as the pin 36.

The pin 36 "keys" the anchor to the shaft and driver so that the anchor cannot be rotated relative to the driver; the pin insures that the anchor can be rotated and maneuvered only with the driver.

The dimensioning of the slots 38 relative to the pin 36 also creates a force fit mating relationship and assembly between the anchor and driver device. The anchor 16 has to be forced onto the end 22 of the shaft by forcing the two ends of the pin 36 through the passageways 40 and into the openings 42. The anchor is resilient and "snaps" into place with the openings 42 on the shaft 36. This frictional or force-fit relationship also helps insure that the anchor and driver device will remain together during positioning and installation of the anchor during surgery.

The anchor is preferably made from Delrin 150SA material, but it can be made of any other equivalent or compatible plastic or surgical material. It is also possible for some applications for the anchor to be made of a bio-absorbable material, such as polyglycolic acid (PGA) or polylactic acid (PLA).

The suture preferably utilized with the present invention is No. USP Size 2 Ticron material made by Davis & Geck Co. It is understood, of course, that any other equivalent suture or other material can be used so long as it satisfies the purposes and objects of the present invention.

A pair of elongated slots or grooves 50 are provided on the shaft 12. (The grooves are best shown in FIGS. 3 and 4). The grooves are positioned 180° apart on the shaft and are of sufficient size and depth to position and retain the suture 18. The grooves 50 are oriented on the driver in axial alignment with the protruding ends of the pin 36 and with the fixation posts 30 and 32. When the anchor 16 is positioned on the driver 10, the suture 18 is tightly pulled into the grooves 50, down the length of the shaft 18 and securely wrapped and affixed around the posts 30 and 32. The ends 26 and 28 of the suture 18 are wound tightly around the fixation posts 30 and 32 which helps to hold the anchor on the driver during use.

After the anchor is positioned and installed in place, the ends of the suture are released from the posts 30 and 32 and the driver is pulled from the site. The fixation of the anchor 16 in the bone or tissue must be sufficiently strong and secure to allow the post 36 to be removed from the slots 38. Once the driver device is removed, the anchor 16 and suture 18 attached thereto are positioned in place for subsequent use during surgery. One such use is to fasten the end of a substitute or synthetic ACL ligament. In general, the anchor can be utilized to attach or reattach soft tissue, ligaments and tendons to bone. In these applications, the anchor would remain permanently in place. Another such use is the isometric testing of a proposed position for installation of an ACL replacement. In this application, the anchor and suture would be removed (and discarded) after the isometric testing was completed. In order to remove the anchor 16, the driver device is again utilized and the installation process reversed.

The shape and configuration of the preferred anchor 16 is best shown in FIGS. 2, 3, 5 and 7. The anchor has a front end or tip 60 which is rounded, conical or pointed for ease of placement and insertion. A sharp pointed anchor would allow it to pierce soft tissue more easily. A plurality of circular ridges 62 extend around the circumference of the anchor and are used to firmly and securely hold the anchor 16 in place in a hole.

When the hole for the anchor 16 is drilled or formed in the bone or tissue, the diameter of the drill should be slightly less than the outer diameter of the ridges 62. In this manner, the anchor 16 can be forced into position in the hole and the compression and friction caused by the ridges 62 against the inner walls of the hole will hold it firmly in place.

Preferably the outer diameter of the ridges is 0.169 inches and the length of the anchor is 0.410 inches. The socket 34 has a diameter of 0.078 inches and a depth of 0.100 inches. The diameter of the end projection 22 is preferably 0.076–0.077 inches and the length of the pin 36 is 0.097 inches. The passageway of the slots 38 has a width of 0.025 inches and the pin 36 has a diameter of 0.0313 inches. The overall length of the driver device 10 (handle and shaft) is approximately 10 inches. Other sizes and dimensions for the present invention can also be utilized.

Three ridges 62 are shown on the anchor 16 and utilized in the preferred embodiment for sufficient strength of the anchor and to provide the requisite holding force in the bone or tissue. It is understood, of course, that a greater or lesser number of ridges could be provided in accordance with the present invention so long as the objects and purposes of the present invention are obtained.

After the hole in the bone or tissue is formed (by drilling, for example with a K-wire having a diameter of 0.146 inches), the anchor 16 is "snapped" into position on the end 22 of the shaft of the driver and the suture 18 tightly wound on the fixation posts. The anchor and driver assembly is then maneuvered or moved into position by the surgeon (e.g. arthroscopically), and the tip 60 of the anchor positioned at or in the opening of the hole. The anchor 16 is then forced axially into the hole by, for example, the surgeon tapping on the end of the driver with a mallet or the like. It is not necessary to rotate the assembly in order to install it in position.

Once the anchor is firmly set in place, the ends 26 and 28 of the suture 18 are removed (unwound) from the fixation posts 30 and 32 and the driver is removed from the surgical site. Since the anchor is retained in the hole with a greater force than that required to snap and unsnap the anchor from the pin 36 on the driver, the driver can be removed easily from the anchor by the surgeon. The anchor with suture attached is then used for its intended use.

If the anchor is to be removed after use, or moved to another position, the installation process is repeated in reverse order, as mentioned earlier.

Figure 8:
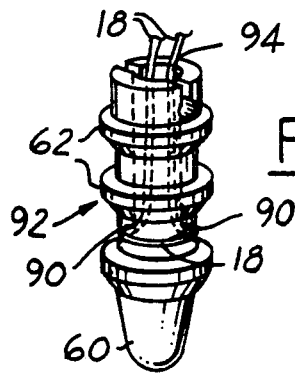
FIGS. 8 and 9 illustrate alternate embodiments of an anchor and driver device.
Figure 9:
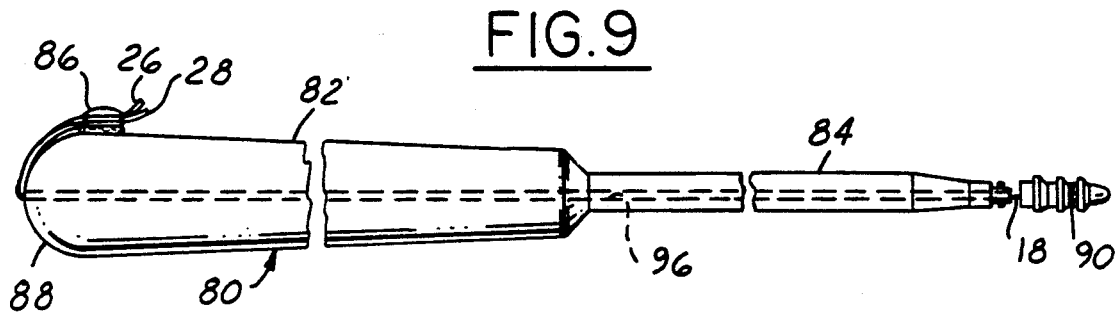

As an alternate embodiment, as shown in FIGS. 8 and 9, the driver device 80, consisting of handle 82 and shaft 84, is cannulated and the suture 18 is passed down the length of the driver and affixed on a fixation post 86 positioned adjacent the end 88 of the handle 82. The suture 18 is passed through opening 90 in anchor 92 and out through the open hollow interior 94 of the anchor. With this embodiment, a suture passer can be utilized to thread the suture through the passageway or channel 96 in the driver 80.

Although particular embodiments of the present invention have been illustrated in the accompanying drawings and described in the foregoing detailed description, it is to be understood that the present invention is not to be limited to just the embodiments disclosed, but that they are capable of numerous rearrangements, modifications and substitutions without departing from the scope of the claims hereafter.

What is claimed is:

1. A device for anchoring a suture to a bone, said device comprising:
   (a) a driver, said driver having a handle and an elongated shaft, said shaft having two ends, one of said ends attached to said handle;
   (b) an anchor member;
   (c) a suture;
   (d) a pair of tab members positioned on the other of said ends of said shaft, said tab member extending radially outwardly from said shaft in a direction substantially normal to the longitudinal axis of said shaft;
   (e) said anchor member having a hollow chamber at one end for receipt of said other of said ends of said shaft in a mating relationship;
   (f) said anchor member having a pair of slots opening into said chamber for receipt of said tab members when said anchor member is positioned on said shaft;
   (g) said suture connected to said anchor member and for attachment to said handle.

2. The device as set forth in claim 1 further comprising attachment means on said handle for securing said suture thereto.

3. The device as set forth in claim 1 further comprising ridge means on said anchor member for assisting in the securing of said anchor member in said bone.

4. The device as set forth in claim 1 further comprising elongated channel means on the exterior surface of said shaft for placement of a portion of said suture extending between said anchor member and said handle.

5. The device as set forth in claim 4 wherein said channel means comprises a pair of opposed channels on said shaft.

6. The device as set forth in claim 1 wherein said suture is positioned in a passageway in said anchor member, said passageway being substantially normal to the longitudinal axis of said anchor member.

7. An anchor and driver assembly comprising:
   (a) a driver;
   (b) an anchor member;
   (c) a suture connected to said anchor member;
   (d) said driver having a handle and an elongated shaft, said shaft having two ends, one of said ends attached to said handle;
   (e) a pair of tab members on said shaft for securing said anchor member on the other end of said shaft, said tab members extending outwardly substantially perpendicular to the longitudinal axis of said shaft, and said anchor member having corresponding slots which mate with said tab members;
   (f) elongated groove means on the exterior surface of said shaft for placement of said suture;
   (g) suture fixation means on said handle;
   (h) wherein when said anchor member is positioned on said driver, said suture is positioned in said groove means and secured to said fixation means.

8. The assembly as set forth in claim 7 wherein said suture is positioned in a passageway in said anchor member, said passageway being substantially perpendicular to the longitudinal axis of said anchor member.

* * * * *